United States Patent [19]

Thoma

[11] Patent Number: 4,551,434

[45] Date of Patent: Nov. 5, 1985

[54] METHOD FOR RECOGNIZING STRUCTURAL INHOMOGENEITIES IN TITANIUM ALLOY TEST SAMPLES INCLUDING WELDED SAMPLES

[75] Inventor: Martin Thoma, Munich, Fed. Rep. of Germany

[73] Assignee: MTU Motoren-und Turbinen-Union Muenchen GmbH, Munich, Fed. Rep. of Germany

[21] Appl. No.: 582,253

[22] Filed: Feb. 22, 1984

[30] Foreign Application Priority Data

Mar. 16, 1983 [DE] Fed. Rep. of Germany ....... 3309448

[51] Int. Cl.$^4$ .......................... G01N 1/32; G01N 33/20
[52] U.S. Cl. .......................................... 436/5; 73/104; 134/7; 134/18; 134/40; 134/41; 156/626; 156/651; 156/664; 356/36; 436/83; 436/174
[58] Field of Search ................. 436/2, 5, 83, 164, 174; 73/104; 156/626, 645, 651, 664; 134/41, 40, 7, 18; 356/36

[56] References Cited

U.S. PATENT DOCUMENTS

| | | | |
|---|---|---|---|
| 2,276,353 | 3/1942 | Thompson | 148/6.2 |
| 2,705,500 | 4/1955 | Deer | 134/40 X |
| 3,514,407 | 5/1970 | Missel | 156/664 X |
| 3,850,712 | 11/1974 | Broughton et al. | 156/664 |
| 3,891,456 | 6/1975 | Hohman et al. | 156/664 X |
| 4,116,755 | 9/1978 | Coggins et al. | 156/664 X |
| 4,289,542 | 9/1981 | Roehl | 134/40 X |
| 4,340,620 | 7/1982 | Mielsch et al. | 427/309 X |
| 4,414,039 | 11/1983 | Thoma | 148/6.2 |

FOREIGN PATENT DOCUMENTS 0261091 1/1970 U.S.S.R. .............................. 156/664

*Primary Examiner*—Arnold Turk
*Assistant Examiner*—Robert J. Hill, Jr.
*Attorney, Agent, or Firm*—W. G. Fasse; D. H. Kane, Jr.

[57] ABSTRACT

Titanium alloy test samples including welded samples of such alloys are tested for recognizing textural or structural faults or flaws in the form of segregations or liquations. To make these flaws visible by increasing the contrast between a flaw and the background, an etching method including two etching steps is used, which achieves especially marked contrasts. The method is based on the selective solution removal of a phase, a grain, or of an impurity of an alloy type. An especially good visual recognition of segregations, liquations or inhomogeneities of welded test samples is made possible by the resulting matte gray surface against which lustrous flaws are clearly visible.

6 Claims, 1 Drawing Figure

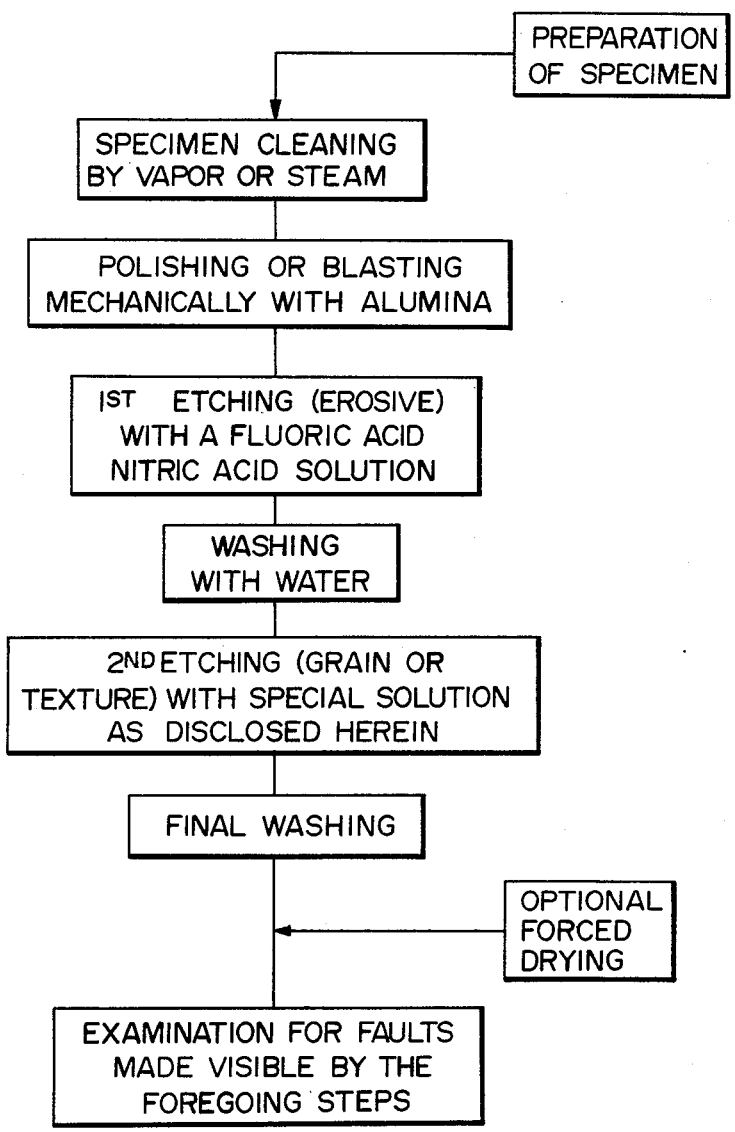

METHOD FOR RECOGNIZING STRUCTURAL INHOMOGENEITIES IN TITANIUM ALLOY TEST SAMPLES INCLUDING WELDED SAMPLES

FIELD OF THE INVENTION

The invention relates to a method for recognizing structural or grain inhomogeneities in the texture of titanium alloy test samples and welded test samples.

BACKGROUND OF THE INVENTION

Titanium alloys may include inhomogeneities in the form of segregates or liquations, which may lead to failure of the structural part or component made of such alloys. Therefore, high load structural parts, such as compressor disks, compressor shafts, and spacing rings in turbo engines, for example, must be free of segregations or liquations. The segregations may be areas of high hardness, caused by oxygen or nitrogen enrichment. There are also, however, soft $\beta$-segregations, which for example show large areas of a $\beta$-alloy concentration or content.

Due to the unacceptability of segregations or liquations in high-load parts, these segregations or liquations must be indicated or made visible. This may be achieved chemically through etching, especially surface etching, in hydrofluoric acid solutions, or electrochemically through anodization in an electrolyte. In the case of chemical etching, the segregation appears light on a dark background. Anodization makes the segregation visible as a dark spot on a light blue colored background. In all methods it is the aim to achieve the maximum possible contrast. However, achieving such high contrast is not always easily possible, depending on the type of alloy and on the segregation or liquation type.

The same problem exists, for instance, in examining resistance spot welds. The metallographic dimensional examining of the resistance weld is carried out, after etching test parts or test samples, by evaluating the resulting weld nugget. Here again, the difficulty lies in achieving a sufficiently marked contrast by the etching of the test sample or test part.

OBJECTS OF THE INVENTION

In view of the above it is the aim of the invention to achieve the following objects singly or in combination:

to provide a method for recognizing structural or grain inhomogeneities of the initially described type, in which large contrasts are achievable on the test sample or specimen through an etching operation, so that inhomogeneities of the grain may easily be made visible;

to make the $\alpha$ and $\beta$ texture distribution visible in a titanium alloy; and to provide a method for exposing segregation or liquation defects in welding samples.

SUMMARY OF THE INVENTION

The method according to the invention for recognizing grain or textural inhomogeneities in titanium alloy test samples, comprises the following steps:

(a) cleaning of the test sample by a steam degreasing operation;

(b) blasting the cleaned test sample surface with Al$_2$O$_3$ (aluminum oxide) particles having a mesh size of about 270;

(c) erosive etching of the test sample with a nitric acid hydrofluoric acid solution;

(d) washing or rinsing the test sample with water;

(e) performing a grain structural or textural etching of the test sample or specimen with a solution including a mixture of chromic acid (CrO$_3$), hydrofluoric acid (HF), and an additive (A) in each of these acids, said additive being selected from the group consisting of arsenic (As) compounds, or antimony (Sb) compounds, or silicon (Si) compounds, whereby the following molar ratios are present:

$8 \geqq F/A \geqq 5$ with regard to fluorine and, $6 \geqq Cr/A \geqq 3$ with regard to chromium, and wherein the molar concentration range for said additive (A) is 0.1 to 2.0 mole per liter; and (f) washing or rinsing the test sample with water.

The present etching method produces especially marked contrast surfaces based on the selective solution removal of a phase, a grain, or of an impurity of an alloy type. The present method produces a matte gray surface which makes an especially good visibility of, for instance, segregations or liquations. These segregations or liquations stand out with a silvery luster from the gray surface. Simultaneously, the $\alpha$ and $\beta$ grain distribution is made visible. This method is useful for examining weld nuggets.

BRIEF FIGURE DESCRIPTION

In order that the invention may be clearly understood, it will now be described, by way of example, with reference to the single FIGURE which shows a flow diagram of the present method steps.

DETAILED DESCRIPTION OF PREFERRED EXAMPLE EMBODIMENTS AND OF THE BEST MODE OF THE INVENTION

Referring first to the single FIGURE, a test sample or specimen is prepared for example by cutting. The specimen is then cleaned, for example by a steam cleaning operation for degreasing the specimen. Following the steam or vapor cleaning the specimen is mechanically blasted or polished with alumina particles having the above mentioned mesh size. After the polishing or blasting the first etching is performed as a corrosive etching with fluoric acid, preferably with a mixture of nitric and fluoric acid. After the corrosive etching the specimen is washed or rinsed again with water whereupon the second etching is performed as a grain structure or textural etching by means of the special solution disclosed above. After the second etching the specimen is again washed or rinsed and dried, if desired, whereupon it is ready for examination or inspection.

The above steps yield good results with respect to the above objectives, especially under the following conditions: the steam degreasing operation takes place in trichloroethene; the aluminum oxide particles are blasted onto a test sample at a pressure of 4 to 5 bar; and the erosive etching is carried out with a nitric acid-hydrofluoric acid solution, of which the concentration comprises 400 g/l of HNO$_3$ and 5 g/l of HF, whereby the etching duration is between 2 and 20 minutes providing especially advantageous erosive etching results. The grain or texture etching is preferably carried out at temperatures in the range of 40° to 80° C., preferably 40° C. to 50° C. in the following baths.

Bath: A (for grain or texture etching)

The grain or texture etching is performed in a solution of $CrO_3/HF/H_2SiF_6$, whereby the molar proportions of $CrO_3$, HF, and $H_2SiF_6$ are chosen corresponding to the molar ratios and the molar concentration set forth below.

Bath: B (for grain or texture etching)

The grain or texture etching may also be performed in a solution similar to Bath: A, but with the fluosilicic acid $H_2SiF_6$ replaced by antimony trioxide $Sb_2O_3$ or by antimony trifluoride $SbF_3$ or by arsenic trioxide $As_2O_3$, whereby the percentage proportions of $CrO_3$, HF and $Sb_2O_3$ or $SbF_3$ or $As_2O_3$ are chosen corresponding to molar ratios and the molar concentration set forth below.

In the above bath the molar ratios are as follows:
$8 \geq F/Sb \geq 5$, or
$8 \geq F/Si \geq 5$, or
$8 \geq F/As \geq 5$; and
$6 \geq Cr/Sb \geq 3$, or
$6 \geq Cr/Si \geq 3$, or
$6 \geq Cr/As \geq 3$, and
the mole concentrations for antimony (Sb), or silicon (Si), or arsenic (As) are within the range of 0.1 to 2.0 mole per liter. The components or compounds providing the antimony, or silicon, or arsenic are collectively referred to herein as additive A.

The object of the invention is also achieved in connection with welded test samples or specimens by etching of a weld nugget, if the welded test sample or specimen undergoes the following method steps in the following order and under the following treatment conditions.

| Method Step | Treatment Conditions | | |
|---|---|---|---|
| | Time (Min) | Material | Temperature (°C.) |
| Wet Grinding | | $Al_2O_3$ grain size about 240 mesh | |
| Pickling | 10 | Solution I $HNO_3/HF$ 400 g/l | 20 |
| Washing or Rinsing | 0.25 | $H_2O$ | 20 |
| Etching | 5–15 | Solution II $CrO_3/HF/H_2SiF_6$ 3 mole/0.6 mole/1.2 mole | 60 |
| Washing | 1 | $H_2O$ | 20 |
| Drying | | Pressurized Air | |

The surface of the welded test sample or specimen to be examined after treatment as set forth above provides a marked contrast as a result of the above steps and conditions, whereby an evaluation of the entire welding spot is now possible.

In a specific example for treating a specimen the above mentioned steam degreasing was performed in trichloroethene ($CHClCCl_2$). Then the test sample was blasted with a flow of aluminum oxide $Al_2O_3$ particles having a mesh size of 270 at a pressure of 4–5 bar. The following pickling or erosion etching operation lasted for 15 minutes in an $HNO_3/HF$ solution at a concentration of 400 g per liter of $HNO_3$ 5 g per liter of HF. After washing or rinsing, the grain or texture etching was carried out, with a $CrO_3/HF/H_2SiF_6$ solution with a molar ratio of 1.8 to 0.3 to 0.6 moles. Then the test sample was washed again and dried. The erosion etching in $HNO_3/F$ resulted in an erosion of 2–4 μm after a 15 minute pickling operation. The erosion after the grain structural or textural etching in the solution of $CrO_3/HF/H_2SiF_6$ amounted to approximately 2 μm.

Although the invention has been described with reference to specific example embodiments, it will be appreciated that it is intended to cover all modifications and equivalents within the scope of the appended claims.

What is claimed is:

1. A method for visually inspecting a test specimen made of titanium alloy for grain or textural inhomogeneities in said test specimen made of titanium alloy, comprising the following steps:
   (a) cleaning a specimen made of titanium alloy by a steam degreasing operation;
   (b) blasting the cleaned surface of the specimen with aluminum oxide ($Al_2O_3$) particles having a mesh size of about 270;
   (c) erosive etching of the specimen with a nitric acid ($HNO_3$)—hydrofluoric acid (HF) solution;
   (d) washing or rinsing the specimen with water;
   (e) grain or texture etching the test specimen with a solution including a mixture of chromic acid ($CrO_3$) and hydrofluoric acid (HF) wherein each of these acids includes hexafluosilicic acid ($H_2SiF_6$) as an additive A in the molar ratio range of $8 \geq F/A \geq 5$ with regard to fluorine and in the molar ratio range of $6 \geq Cr/A \geq 3$ with regard to chromium, and wherein the molar concentration range for said additive A is 0.1 to 2.0 mole per liter;
   (f) washing or rinsing the specimen with water, whereby contrast between any grain or textural inhomogeneities and their background is substantially increased for said visual inspection, and
   (g) then visually inspecting the specimen for any grain or textural inhomogeneities.

2. The method of claim 1, wherein said grain or texture etching is performed in a temperature range of 40° C. to 80° C.

3. The method of claim 1, wherein said erosive etching solution of nitric acid-hydrofluoric acid has a concentration of 400 g/l of $HNO_3$ and 5 g/l of HF.

4. The method of claim 3, wherein said grain or texture etching takes place at a temperature of 40° C. to 80° C.

5. A method for visually inspecting a titanium alloy weld nugget for grain or textural inhomogeneities in said titanium alloy weld nugget, comprising the following steps:
   (a) wet grinding a titanium alloy weld nugget with grinding material having a mesh size of about 240;
   (b) pickling or corrosion etching the specimen for about 10 minutes in a first solution of nitric acid ($HNO_3$) and hydrofluoric acid (HF) having a concentration ratio of 400 g/liter of $HNO_3$ to 5 g/liter of HF at a temperature of about 20° C.;
   (c) rinsing the pickled specimen in water for about 15 seconds at a water temperature of about 20° C.;
   (d) grain or texture etching the rinsed specimen in a second solution of chromic acid ($CrO_3$), hydrofluoric acid (HF), and Hexafluosilicic acid ($H_2SiF_6$) with molar ratios of $CrO_3$ to HF to $H_2SiF_6$ corresponding to 3 mole to 0.6 mole to 1.2 mole at a temperature of about 60° C.;
   (e) rinsing the specimen in water for about 60 seconds, said water having a temperature of about 20° C., and (f) drying the specimen with pressurized air, whereby contrast between any textural inhomogeneities and their background is substantially increased for said visual inspection, and (g) visually inspecting the titanium alloy weld nugget for any grain or textural inhomogeneities.

6. The method of claim 5, wherein said grinding material is aluminum oxide ($Al_2O_3$).

* * * * *